United States Patent [19]

Batzar

[11] 4,115,143

[45] Sep. 19, 1978

[54] DUST-FREE THERMALLY STABLE LEAD CHROMATE PIGMENT COMPOSITION AND PROCESS OF PREPARATION

[75] Inventor: Kenneth Batzar, Piscataway, N.J.

[73] Assignee: E. I. Du Pont de Nemours and Company, Wilmington, Del.

[21] Appl. No.: 808,995

[22] Filed: Jun. 22, 1977

Related U.S. Application Data

[63] Continuation-in-part of Ser. No. 690,937, May 28, 1976, abandoned.

[51] Int. Cl.$^2$ .................................................. C09C 1/20
[52] U.S. Cl. .................................. 106/298; 106/308 Q
[58] Field of Search ................ 106/298, 308 F, 308 Q

[56] References Cited

U.S. PATENT DOCUMENTS

| | | | |
|---|---|---|---|
| 3,470,007 | 9/1969 | Linton | 106/298 |
| 3,649,321 | 3/1972 | Durrant | 106/308 F |
| 3,928,060 | 12/1975 | Smith et al. | 106/308 Q |
| 3,973,982 | 8/1976 | Bingham | 106/308 Q |

*Primary Examiner*—Winston A. Douglas
*Assistant Examiner*—J. V. Howard

[57] ABSTRACT

Substantially non-dusting, thermally stable lead chromate pigment composition consisting essentially of lead chromate pigment and at least one organic ester selected from esters of phthalic and terephthalic acids and esters of fatty acids and process of preparation by forming a mixture of lead chromate pigment and water and intimately contacting the mixture with at least one organic ester. The lead chromate pigment composition can be poured, packaged, or otherwise processed in dry form with the formation of far less dust in the work environment than is encountered using conventional lead chromate pigment and exhibits high thermal stability in plastics.

8 Claims, 2 Drawing Figures

FIG. 1
FIG. 2
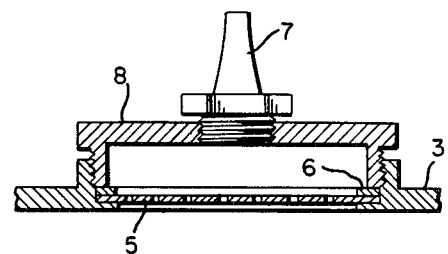
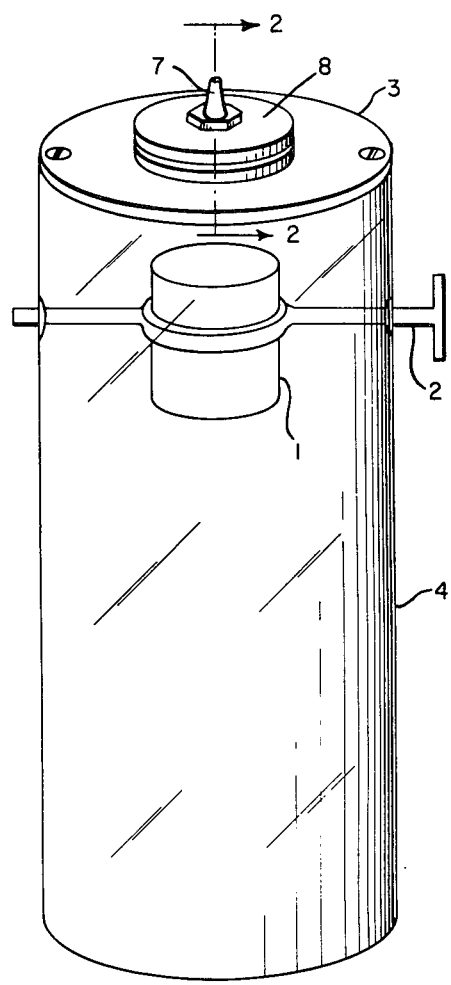

DUST-FREE THERMALLY STABLE LEAD CHROMATE PIGMENT COMPOSITION AND PROCESS OF PREPARATION

CROSS REFERENCE TO RELATED APPLICATION

This application is a continuation-in-part of my co-pending application Ser. No. 690,937, filed May 28, 1976, now abandoned.

BACKGROUND OF THE INVENTION

This invention relates to metal chromate pigment compositions and, more particularly, to substantially non-dusting thermally stable lead chromate pigment compositions and their preparation.

Metal chromate pigments have been known and widely used for many years, and are available in a broad range of shades from very green shade yellows to yellowish reds. Of the various metal chromate pigments, e.g., strontium chromate, zinc chromate, and lead chromate, lead chromate is the most widely used. These chromate pigments are relatively inexpensive to manufacture and have generally good tinctorial properties.

Thermal stability, i.e., resistance to darkening at elevated temperatures in contact with thermoplastics, and chemical resistance of lead chromate pigments have been improved markedly by the application of coatings of hydrous oxides such as silica and alumina to the base or uncoated metal chromate pigment, as described for example in Linton U.S. Pat. No. 3,370,971. To improve the mechanical strength of the coated metal chromate pigments, alkaline earth metal salts of rosin acids and of long-chain fatty acids have been applied to the pigments, as described in Linton U.S. Pat. No. 3,470,007.

Metal chromate pigments, though manufactured in aqueous systems, are commonly dried to a powder prior to shipment and use in coating compositions. Packaging, pouring and otherwise handling the dry pigment can create a dusting problem in the immediate work environment. If the dust level is sufficiently high, special protective equipment may be necessary to insure proper worker safety. With increased industry and government concern over protection of the environment and worker health, it is highly desirable to have a dry chromate pigment which is substantially dust-free. The resulting elimination of the need for special protective equipment can cut the cost of pigment to the manufacturer and user and insure worker safety with less monitoring and inconvenience than is currently employed.

In addition to dusting problems, the thermal stability of conventional lead chromate pigments, while improved, is not sufficiently high for particularly demanding applications in thermoplastics. This is particularly true under conditions of exceptionally high temperature processing.

This invention provides for substantially dust-free lead chromate pigment which exhibits all the desirable properties common to conventional lead chromate pigments and exhibits much higher thermal stability.

SUMMARY OF THE INVENTION

According to this invention there is provided a lead chromate pigment composition consisting essentially of from 75 to 98% by weight, and preferably from 85 to 92% by weight, of a lead chromate pigment, based on the weight of the lead chromate pigment composition and from 2 to 25% by weight, and preferably from 8 to 15% by weight, based on the weight of lead chromate pigment composition, of at least one organic ester selected from esters of phthalic and terephthalic acid of the formula

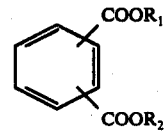

where $R_1$ and $R_2$ are each independently selected from alkyl of 3 to 20 carbon atoms, benzyl of the formula

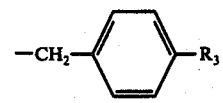

where $R_3$ is selected from —H, —$SO_3H$, and

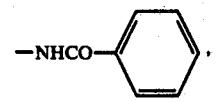

and esters of fatty acids of the formula

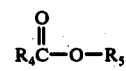

where $R_4$ is alkyl of 5 to 20 carbon atoms and $R_5$ is an alkyl of 2 to 10 carbon atoms.

The lead chromate pigment composition is preferably prepared by the steps of (i) forming a mixture consisting essentially of from 1 to 80% by weight of lead chromate pigment, based on the weight of the mixture, and from 20 to 99% by weight of water, based on the weight of the mixture, (ii) intimately contacting the mixture of step (i) with from 2 to 25% by weight, based on the weight of the lead chromate pigment, of at least one organic ester selected from esters of phthalic and terephthalic acid of the formula

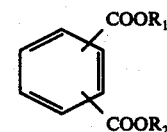

where $R_1$ and $R_2$ are each independently selected from alkyl of 3 to 20 carbon atoms, benzyl of the formula

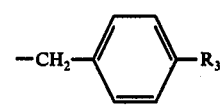

where $R_3$ is selected from —H, —$SO_3H$, and

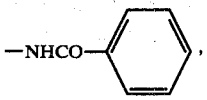

and esters of fatty acids of the formula

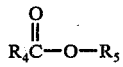

where $R_4$ is alkyl of 5 to 20 carbon atoms and $R_5$ is an alkyl of 2 to 10 carbon atoms.

(iii) isolating the lead chromate pigment composition.

This invention further provides for an apparatus for determining, either qualitatively or quantitatively, the level of dust which arises from a given quantity of dry particulate solid, referred to herein as the dust index, comprising a first container having an opening in the top, a porous member detachably fitted to the opening in the top of the first container, a rotatable shaft, mounted transversely with respect to the first container, supporting a second container, the second container being smaller than the first container and coaxially disposed with respect to the first container, the axis of the shaft being positioned between the top of the first container and the bottom of the first container to allow the second container to rotate within the first container, and means for applying a vacuum to the opening in the top of the first container.

DESCRIPTION OF THE DRAWING

FIG. 1—apparatus for determining the dust index of a particulate solid.

FIG. 2—cross-sectional view of the top of the apparatus.

DETAILED DESCRIPTION OF THE INVENTION

The lead chromate pigments included in the composition of the invention are in the form of base or uncoated lead chromate pigment including the known after-treatment of hydrous oxides, such as silica and alumina, as described in U.S. Pat. No. 3,370,971. Lead chromate pigments are preferred because of their widespread use in the industry and their excellent tinctorial properties. The preferred lead chromate pigments are available in a broad range of shades. On the one hand there is a very green shade "Primrose Yellow" in rhombic crystal form. A relatively pure lead chromate in monoclinic crystal form is much redder and is commonly known as "Medium Yellow". Intermediate shades of lead chromate pigment are available in solid solutions of lead chromate and lead sulfate usually in monoclinic form. At the other color extreme is a series of solid solutions of lead chromate, lead sulfate and lead molybdate which are oranges or even yellowish reds commonly known as "Molybdate Oranges" or "Molybdate Reds".

The organic ester component of the compositions of the invention which are preferred include dialkyl esters of phthalic acid wherein the alkyl groups contain 4 to 8 carbon atoms, such as di-2-ethylhexyl phthalate, and alkyl benzyl esters of phthalic acid, such as butyl benzyl phthalate. The preferred esters of fatty acids contain from 12 to 18 carbons in the alkyl group of the fatty acid and from 3 to 8 carbon atoms in the ester alkyl group, such as butyl stearate. The amount of organic ester in the composition varies according to the particular ester employed and the end use for which the pigment composition is intended. For example, if the pigment composition is to be used as a colorant for plastics, where only a relatively small quantity of pigment is commonly used, as high as 25% by weight of organic ester can be present in the pigment composition. In practice, it is preferred for most uses that the pigment composition contain at least 2% by weight of at least one organic ester to render the dry particulate solid substantially dust-free. Using more than 25% by weight of organic ester contributes little, if any, to the further decrease in dusting or increase the thermal stability and is not recommended. Such higher levels may adversely affect the properties of the metal chromate pigment composition in use and cause the formation of plastic-like masses if the pigment composition is pulverized. For most applications 10 to 15% by weight of organic ester is preferred.

To insure that the lead chromate pigment composition of the invention remains substantially dust-free during dry handling, the melting point of the organic ester or mixture of organic esters which are present in the composition should be below the temperature at which the composition is handled in the dry state. In most cases the dry composition is handled at ambient temperature, e.g., 15°–25° C. Consequently, a melting point of 15° C. or less is satisfactory for the organic ester component of the composition.

In the event that the melting point of a particular organic ester of choice is higher than desired, mixtures of esters can be formulated within the level of one skilled in the art to lower the melting point of the organic ester component to the desired level. For example, the melting point of n-butyl stearate is 19°–24° C., which may be too high for many work environments. A mixture of n-butyl stearate and isobutyl stearate which has a melting point several degrees lower will exhibit this melting point depression depending upon the relative amounts of each component used. The same is true for di-n-octylphthalate versus a mixture of di-n-octylphthalate and di-2-ethylhexyl phthalate.

To prepare the lead chromate pigment composition of the invention a mixture of lead chromate pigment in aqueous medium is intimately contacted with at least one organic ester, preferably from 10 to 15% by weight, based on the weight of the lead chromate pigment. The relative amounts of pigment and water can be such that the mixture is in the form of an aqueous slurry of pigment, for which the mixture can contain from 1 to 35% by weight of pigment, based on the weight of the mixture, and from 65 to 99% by weight of water, based on the weight of the mixture. Alternatively the mixture can be in the form of an aqueous presscake which, for example, normally results when the lead chromate pigment is isolated by filtration from the aqueous medium in which it was synthesized. In the case of a presscake, the mixture can contain from 25 to 80% by weight of lead chromate pigment, based on the weight of the mixture, and from 20 to 75% of water, based on the weight of the mixture.

Formation of the lead chromate pigment composition is best achieved by promoting intimate contact of the pigment/water mixture and the organic ester. Intimate contact can be conveniently and effectively achieved by subjecting the pigment/water mixture and the organic ester to agitation, stirring or emulsification. Common devices to effect such contact include conventional blenders, and, in general, containers equipped with high speed agitators. The organic ester can be contacted with the pigment/water mixture as such or the organic ester can first be emulsified in water prior to contact with the pigment/water mixture. The latter procedure is preferred as it insures homogeneous distribution of the organic ester throughout the metal chromate pigment.

Although the temperature of contact is not particularly critical, it is preferred that the temperature be from 80° to 95° C. to insure complete association of the organic ester with the metal chromate pigment. This temperature range is further preferred for the sake of convenience, since the aqueous pigment slurries in which lead chromate pigments are synthesized are commonly within this temperature range prior to isolation of the pigment. Consequently, without first isolating the pigment from the synthesis slurry, the pigment slurry can be directly used in the process of the invention to prepare the lead chromate pigment composition.

As stated above the lead chromate pigment composition can be prepared directly from a synthesis slurry of base of uncoated pigment or of coated pigment, i.e., pigment coated with hydrous oxides such as silica and alumina, as described in U.S. Pat. No. 3,370,971. A major factor governing the point during the processing of the pigment where formation of the pigment composition is desirable is the point at which the pigment is handled dry and dust control is a problem. For example, when the base or uncoated pigment is isolated from the synthesis slurry and dried prior to application of a coating, as described above, the pigment composition should preferably be formed prior to drying and subsequent application of the coating. The practice of the invention does not interfere with the subsequent application of coating or other conventional aftertreatments. To insure dust control after further processing of the pigment, e.g., application of coating, it is preferred that the further processing or coated pigment again be mixed with water and intimately contacted with an organic ester in accordance with the invention.

The metal chromate pigment composition, in which pigment and organic ester are believed to form cohesive discrete particles of the composition, can be isolated from the aqueous slurry in any conventional manner. For example, the slurry can be flocculated, if necessary, with such flocculating agents as aluminum sulfate, filtered, washed with water and dried at ambient or elevated temperatures.

The isolated dry lead chromate pigment composition can be packaged, poured, or otherwise handled without substantial formation of dust.

To determine the level of dusting or dust index of the dry particulate lead chromate pigment composition, and the level of dusting of particulate solids generally, the device shown in FIGS. 1 and 2 is utilized. Referring to FIG. 1, a quantity of particulate solid is placed in internal container 1 which is mounted to rotatable shaft 2. A housing 3 for a porous member and nozzle for a vacuum line is securely attached to cover the opening in external container 4. FIG. 2 shows a cross-sectional view of housing 3. Referring to FIG. 2, porous member 5 is placed in the opening in housing 3. The size of the pores in the porous member should be small enough to prevent passages therethrough of particles of the solid to be tested. For the lead chromate pigment composition of the invention conventional white filter paper, e.g., Whatman #2, is preferred. To insure that the filter paper remains in place during the determination, a metal ring 6, is placed on top of the filter paper. A nozzle 7 is then attached to nozzle housing 8 which is securely fitted to housing 3. A vacuum line, not shown, can be attached to nozzle 7.

To determine the dust index the internal container 1 is rapidly inverted by rotating the shaft 2. Three seconds after inverting the container a vacuum of from 55 to 65 mm of Hg is drawn for 10 seconds on the external container 4 through nozzle 7. In this manner the particulate solid which is still suspended in the atmosphere of the external container 1 is drawn to the porous member 5 and is deposited thereon as the vacuum is drawn. The nozzle housing 8 is then removed from the top of external container 4 and the porous member is removed. A relatively accurate and highly reproducible qualitative determination of the dust index can be determined by visual examination of the porous member. Since the lead chromate pigment composition is highly colored, even minute quantities will impart some color to the porous member. A highly colored porous member is indicative of a high dust index whereas a very faintly colored or noncolored porous member is indicative of a low dust index; in other words a substantially dust-free particulate solid.

Although it is believed that the qualitative determination described above is a highly satisfactory indication of a given dust index, the amount of dust generated by a given quantity of pigment can of course be determined by destruction of the filter paper and pigment with subsequent analysis, for example, by atomic absorption. In any case, comparative determinations should be made using the same amount of particulate solid, same hold time after inversion of the internal container, and same amount of vacuum to provide a controlled comparison.

When tested for dusting as described above, the metal chromate pigment composition of the invention shows at most only very faint coloration of the porous member and is consequently substantially dust-free. Metal chromate pigments known in the art show extreme coloration of the porous member when comparably tested.

Like conventional lead chromate pigments, the metal chromate pigment composition of the invention is useful as a pigment for a wide variety of applications. For example the composition can be directly incorporated in plastics or coating compositions, such as oil or water base paints in the conventional manner to impart color thereto.

When the lead chromate pigment composition is made using a hydrous oxide coated lead chromate, the compositions of the invention are particularly useful as colorants for a wide variety of thermoplastics, because they exhibit exceptionally high thermal stability, i.e., resistance to darkening, at the elevated temperatures utilized in the processing of thermoplastics. In general, when compared with hydrous oxide coated lead chromate pigments which have not been treated with ester in accordance with the invention, the compositions of the invention exhibit color stability at temperatures at least 30° C. higher. In the examples which follow the tests involving plastics applications have been restricted to polystyrene. However, the advantages of this invention are applicable to other thermoplastics, such as polyethylene, polypropylene, nylon acetal resins, polyester resins, polyvinylfluoride, and ABS resin.

The following examples are to illustrate the invention.

EXAMPLE 1

Forty-eight hundred milliliters of an aqueous slurry containing 480 grams of lead chromate pigment of the molybdate orange type coated with 16% by weight of dense amorphous silica is heated to 90° C. In a separate container 10.15 grams of an amine salt of dodecyl benzene sulfonic acid (anionic surfactant) is dissolved in 67.5 grams of dioctyl phthalate. The solution of di-2-ethylhexyl phthalate and surfactant is then added to 350 milliliters of hot water at a temperature of 60° C. in a high-speed blender. The resulting mixture is emulsified at low speed and added slowly with stirring to the heated aqueous slurry prepared above. The slurry is stirred for 15 minutes after the completion of the addition. Then 30 grams of aluminum sulfate is added to the slurry to effect flocculation and the pH is adjusted to 4.0–4.2.

To isolate the product the flocculated slurry is filtered, washed with water to a specific resistance of 5000 ohm-cm and dried at 82° C for 16 hours. The dried product is then pulverized at high speed using a 0.066 screen and yields 546 grams of bright orange pigment.

The product contains 13% by weight of di-2-ethylhexyl phthalate and 87% by weight of lead chromate pigment.

Using the apparatus pictured in FIG. 1, 45 grams on a pigment basis of the lead chromate pigment composition is placed in internal container 1, diameter 5.5 cm. and height 5.5 cm. A filter paper, i.e., Whatman No. 2, and vacuum line are attached to the opening in external container 4, diameter 14 cm. and height to opening 6.35 cm. The internal container 1 is inverted by turning shaft 2 located 24 cm. from the bottom of external container 4. Three seconds after inversion of internal container 1 a vacuum of 60 mm Hg is applied to external container 4 for 10 seconds. The filter paper is then removed and found to exhibit no visible coloration.

Control A

The procedure of Example 1 is followed except that no dioctyl phthalate solution is added to the slurry. The resulting lead chromate pigment is tested exactly as described in Example 1 and the resulting filter paper shows very intense coloration.

EXAMPLE 2

Fifty-one hundred milliliters of an aqueous slurry containing 600 grams of yellow lead chromate pigment is heated to 90° C. In a separate container 13 grams of the surfactant described in Example 1 is dissolved in 65 grams of dioctyl phthalate and emulsified as described in Example 1. The emulsion is added dropwise to the aqueous slurry of pigment over a 2-minute period. Then 75 milliliters of a commercially available polyacrylamide flocculating agent is added to the slurry to effect flocculation.

To isolate the product the flocculated slurry is filtered, washed with water to a specific resistance of 1200 ohm-cm and dried at 104° C. The product is pulverized as described in Example 1 and yielded 662 grams of bright yellow pigment. The product contains 10% by weight of dioctyl phthalate and 90% by weight of yellow lead chromate pigment.

The lead chromate pigment composition is tested exactly as described in Example 1 and the resulting filter paper exhibits very faint yellow coloration.

Control B

The procedure of Example 2 is followed except that no dioctyl phthalate solution is added to the slurry. The resulting lead chromate pigment is tested exactly as described in Example 1 and the resulting filter paper shows very intense yellow coloration.

EXAMPLE 3

One hundred milliliters of water containing 4.5 grams of a commercially available non-ionic surfactant in solution is added dropwise to 30 grams of dibutyl phthalate with agitation and stirred for 5 minutes. The resulting solution is added to a high-speed blender. An aqueous presscake (35–40% by weight of water) containing 150 grams, dry basis, of a lead chromate of the molybdate orange type described in Example 1 is added to the high-speed blender and blended for 10 minutes. The blended mixture is dried at 82° C. for 16 hours and pulverized at high speed using a 0.066 screen.

The resulting bright orange pigment composition is tested for dust as described in Example 1 and the filter paper exhibits no visible coloration.

Control C

The procedure of Example 3 is followed except that the presscake is not treated with the dibutyl phthalate solution. The resulting lead chromate pigment is tested as described in Example 1 and the filter paper shows very intense coloration.

EXAMPLE 4

Four thousand eight hundred and seventy milliliters of an aqueous slurry containing 360 grams of the lead chromate pigment described in Example 1 is heated to 90° C. In a separate container 5.4 grams of the surfactant of Example 1 is dissolved in 54.0 grams of butyl stearate and emulsified as described in Example 1. The resulting emulsion is added dropwise over a period of 2 minutes to the aqueous slurry of pigment with agitation. Then 22 grams of aluminum sulfate is added to the slurry to effect flocculation.

To isolate the product the flocculated slurry is filtered, washed with water to a specific resistance of 2000 ohm-cm and dried at 82° C. The dried product is pulverized as described in Example 1 and yields 413 grams of bright orange pigment.

The product contains 13% by weight of butyl stearate and 87% by weight of lead chromate pigment.

The product is tested for dust as described in Example 1 and the filter paper exhibits no visible coloration.

Control D

The procedure of Example 4 is followed except that no butyl stearate solution is added to the slurry. The resulting lead chromate pigment is tested as described in Example 1 and the filter paper shows very intense coloration.

EXAMPLE 5

Five hundred parts of an aqueous slurry containing 32.5 parts of lead chromate pigment of the molybdate orange type coated with 25% by weight of dense amorphous silica is heated to 92° C. In a separate container 0.5 part of the surfactant described in Example 1 is dissolved in 4.7 parts of a 9:1 mixture of isobutyl:n-butyl stearate. The solution of mixed stearate and surfactant is then added to 26 parts of hot water at a temperature of 60° C. in a high shear mixer. The resulting mixture is emulsified and added slowly with stirring to the heated aqueous slurry prepared above. The slurry is stirred for 15 minutes after completion of the addition. Then 4.3 parts of aluminum sulfate is added to the slurry to effect flocculation and the pH is adjusted to 4.0–4.2.

To isolate the product the flocculated slurry is filtered, washed with water to a specific resistance of 2000 ohm-cm and dried at 82° C. for 24 hours. The dried product is then pulverized at high speed using a ⅛ inch screen and yields 47 parts of bright orange pigment.

The product is found to contain 9.5% by weight of mixed butyl stearate and 86.5% by weight of silica coated lead chromate pigment.

The pigment is then tested in the following manner for thermal stability, i.e., resistance to darkening, in plastics. A mixture of 1100 grams of commercially available polystyrene pellets and 12.1 grams of the pigment prepared above are placed in a container and rolled for 10 minutes at a peripheral speed of 117 feet/minute. The mixture is then placed in a Banbury mixer, a commercially available high melt shear blender, which was preheated by mixing a charge of 1100 grams of polystyrene for two minutes at high speed. The Banbury mixer is run at high speed at 260° F. (126.7° C.) until the mixture fluxes, i.e., appears at a semi-solid mass (at approximately 1° to 6° C.). Then mixing is continued at 300° F. (149° C.) for 3 minutes. The mixture is cooled and chopped into granules. The granules are injection molded at temperatures of 400° F. (204.4° C.), 450° F. (232° C.), 500° F. (260° C.), 550° F. (288° C.), and 600° F. (315.5° C.). The dwell time at 400° F. (204.4° C.) is 3 minutes and the dwell time at the remaining temperatures 10 minutes.

The resulting molded plastic chips shows no significant darkening at 450° F. (232° C.), slight darkening at 500° F. (260° C.) and 550° F. (288° C.), and moderate darkening at 600° F. (315.5° C.).

Control E

The procedure of Example 5 is followed except that no mixed butyl stearates are added to the slurry. The resulting lead chromate pigment is tested for thermal stability exactly as described in Example 5 except that 11.0 grams of pigment are blended with the 1100 grams of polystyrene so that the amount of color in the blend is the same.

The molded plastic chips show slight darkening at 450° F. (232° C.), moderate darkening at 500° F. (260° C.), and significant darkening at 550° F. (288° C.) and 600° F. (315.5° C.).

EXAMPLE 6

Five hundred forty parts of an aqueous slurry containing 33.5 parts of lead chromate of the molybdate orange type coated with 20.5% by weight of dense amorphous silica is heated to 92° C. In a separate container 0.5 part of the surfactant described in Example 1 is dissolved in 4.7 parts of a 9:1 mixture of isobutyl:n-butyl stearate. The solution of mixed stearate and surfactant is then added to 31 parts of hot water at a temperature of 60° C. in a high shear mixer. The resulting mixture is emulsified and added slowly with stirring to the heated aqueous slurry prepared above. The slurry is stirred for 15 minutes after completion of the addition. Then 2.5 parts of aluminum sulfate is added to the slurry to effect flocculation and the pH is adjusted to 4.0–4.2.

To isolate the product the flocculated slurry is filtered, washed with water to a specific resistance of 2000 ohm-cm and dried at 82° C. for 24 hours. The dried product is then pulverized at a high speed using a ⅛ inch screen and yields 46 grams of bright orange pigment.

The product is found to contain 9.5% by weight of mixed butyl stearate and 88% by weight of silica coated lead chromate pigment.

The pigment is tested for thermal stability as described in Example 5. The resulting molded plastic chips show no significant darkening at 450° F. (232° C.), slight darkening at 500° F. (260° C.), and moderate darkening at 550° F. (288° C.).

Control F

The procedure of Example 6 is followed except that no mixed butyl stearates are added to the slurry. The resulting lead chromate pigment is tested for thermal stability as described in Example 5 except that 11 grams of pigment are blended with the 1100 grams of polystyrene so that the amount of color in the blend is the same.

The molded plastic chips show slight darkening at 450° F. (232° C.) and significant darkening at 500° F. (260° C.) and 550° F. (288° C.).

What is claimed is:

1. Lead chromate pigment composition consisting essentially of from 75 to 98% by weight of lead chromate pigment, based on the weight of the composition, and from 2 to 25% by weight, based on the weight of the composition, of at least one organic ester selected from esters of phthalic and terephthalic acid of the formula

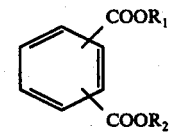

where $R_1$ and $R_2$ are each independently selected from alkyl of 3 to 20 carbon atoms, benzyl of the formula

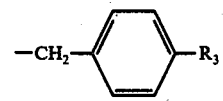

where $R_3$ is selected from —H, —SO$_3$H, and

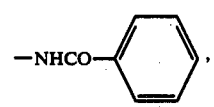

and esters of fatty acids of the formula

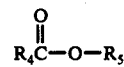

where $R_4$ is alkyl of 5 to 20 carbon atoms and $R_5$ is an alkyl of 2 to 10 carbon atoms.

2. Lead chromate pigment composition according to claim 1 consisting essentially of from 85 to 92% by weight of a lead chromate pigment, based on the weight of the composition and from 8 to 15% by weight of organic ester, based on the weight of the composition.

3. Lead chromate pigment composition according to claim 1 wherein the organic ester is selected from di-2-ethylhexyl phthalate, butyl benzyl phthalate, and butyl stearate.

4. Process for preparing a lead chromate pigment composition by the steps of
(i) forming a mixture consisting essentially of from 1 to 80% by weight of lead chromate pigment, based on the weight of the mixture, and from 20 to 99% by weight of water, based on the weight of the mixture;
(ii) intimately contacting the mixture of step (i) with from 2 to 25% by weight, based on the weight of the lead chromate pigment, of at least one organic ester selected from esters of phthalic and terephthalic acid of the formula

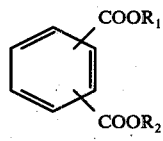

where $R_1$ and $R_2$ are each independently selected from alkyl of 3 to 20 carbon atoms, benzyl of the formula

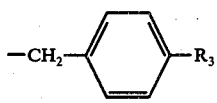

where $R_3$ is selected from —H, —SO$_3$H, and

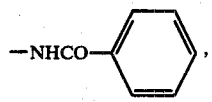

and esters of fatty acids of the formula

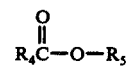

where $R_4$ is alkyl of 5 to 20 carbon atoms and $R_5$ is an alkyl of 2 to 10 carbon atoms;
(iii) isolating the lead chromate pigment composition.

5. Process according to claim 4 wherein the mixture of step (i) consists generally of from 5 to 35% by weight of lead chromate pigment, based on the weight of the mixture, and from 65 to 95% of water, based on the weight of the mixture.

6. Process according to claim 4 wherein the mixture of step (i) consists essentially of from 25 to 80% by weight of lead chromate pigment, based on the weight of the mixture, and from 20 to 75% of water, based on the weight of the mixture.

7. Process according to claim 4 wherein the organic ester is selected from the group consisting of di-2-ethylhexyl phthalate, butyl benzyl phthalate, and butyl stearate.

8. Process according to claim 4 wherein the organic ester of step (ii) is in an amount from 10 to 15% by weight, based on the weight of the lead organic pigment of step (i).

* * * * *

UNITED STATES PATENT OFFICE
CERTIFICATE OF CORRECTION

PATENT NO. : 4,115,143
DATED : September 19, 1978
INVENTOR(S) : Kenneth Batzar

It is certified that error appears in the above–identified patent and that said Letters Patent are hereby corrected as shown below:

Column 12, line 17, "generally" should be --essentially--.

Column 12, line 32, "organic" should be --chromate--.

Signed and Sealed this

Tenth Day of April 1979

[SEAL]

Attest:

RUTH C. MASON
Attesting Officer

DONALD W. BANNER
Commissioner of Patents and Trademarks